(12) United States Patent
Hastings et al.

(10) Patent No.: US 6,349,143 B1
(45) Date of Patent: Feb. 19, 2002

(54) METHOD AND SYSTEM FOR SIMULTANEOUSLY DISPLAYING DIAGNOSTIC MEDICAL ULTRASOUND IMAGE CLIPS

(75) Inventors: Jeffrey S. Hastings, Los Altos; Jonathan Bernard, Santa Clara, both of CA (US); David A. Rock, Saline, MI (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/200,170

(22) Filed: Nov. 25, 1998

(51) Int. Cl.$^7$ ................................................. G06K 9/00
(52) U.S. Cl. ..................................................... 382/128
(58) Field of Search ............................... 382/128, 132, 382/232; 128/915, 916, 920, 922; 345/1, 4; 348/185; 600/437, 440, 441

(56) References Cited

U.S. PATENT DOCUMENTS

| | | | | |
|---|---|---|---|---|
| 4,817,433 A | * | 4/1989 | Sato | 73/620 |
| 4,869,256 A | * | 9/1989 | Kanno et al. | 600/440 |
| 5,107,844 A | * | 4/1992 | Kami et al. | 600/463 |
| 5,235,510 A | | 8/1993 | Yamada et al. | 600/300 |
| 5,274,759 A | | 12/1993 | Yoshioka | 600/440 |
| 5,367,318 A | * | 11/1994 | Beaudin et al. | 345/508 |
| 5,510,832 A | * | 4/1996 | Garcia | 348/56 |
| 5,616,930 A | * | 4/1997 | Janssens et al. | 250/584 |
| 5,619,995 A | | 4/1997 | Lobodzinski | 600/425 |
| 5,687,717 A | * | 11/1997 | Halpern et al. | 600/300 |
| 5,690,111 A | * | 11/1997 | Tsujino | 600/440 |

OTHER PUBLICATIONS

"International Search Report for corresponding PCT Application PCT/US99/25396".

TomTec Imaging Systems Manual P/N 070300200 A, pp. 11–13.

TomTec Imaging Systems Manual P/N 070300200 A, pp. 35–37.

TomTec Imaging Systems Manual P/N 070300300 A, pp. 11–14.

* cited by examiner

*Primary Examiner*—Andrew W. Johns
*Assistant Examiner*—Shervin Nakhjavan
(74) *Attorney, Agent, or Firm*—Brinks Hofer Gilson & Lione

(57) ABSTRACT

The preferred embodiments include a method and system for simultaneously displaying diagnostic medical ultrasound image clips on one or more monitors without degradation in display frame rate. In one preferred embodiment, compressed ultrasound image frames are sent to a video display system for decompression. Because compressed image frames are sent, there is no degradation in frame rate caused by the bandwidth limitations of the CPU/video display system bus. Further, because the video display system decompress the compressed image frames faster than decompression software executed by a CPU, there is no degradation in frame rate caused by power limitations of the CPU. The video display system can also be used to control the frame rate, luminance, and size of individual ultrasound image clips. The preferred video display system described herein finds particular utility in ultrasound examinations performed in cardiac, radiological, obstetrical, and neo-natal ultrasound examinations.

13 Claims, 4 Drawing Sheets

METHOD AND SYSTEM FOR SIMULTANEOUSLY DISPLAYING DIAGNOSTIC MEDICAL ULTRASOUND IMAGE CLIPS

BACKGROUND

Recently, ultrasound image clips (i.e., a series of ultrasound image frames) have been stored in a digital format for playback on an ultrasound image review system, such as an ultrasound image review station. In some image review systems, a CPU transfers ultrasound image clips stored in a memory unit to a video display system (e.g., a video display card), which formats the image clips for display on a monitor. Multiple video display systems can be used to display image clips on multiple monitors. In many medical applications, it is important to display the frames of an ultrasound clip at the same rate at which the frames were originally acquired. However, hardware limitations of the ultrasound review system often result in the display of ultrasound image clips at a lower frame rate, especially when multiple ultrasound image clips are displayed on one or more monitors.

Some ultrasound image clips require a bus bandwidth of 30 MB/sec to be displayed at full frame rate. Since the bandwidth of a standard peripheral component interconnect (PCI) bus between the CPU and the video display system is typically about 60 MB/sec, only two ultrasound image clips can be displayed per monitor without a degradation in frame rate. Although some review systems have an accelerated graphics port (AGP) with a bandwidth of about 120 MB/sec that can be used to display up to four ultrasound image clips without frame rate degradation, there is only one AGP bus per review station. Thus, by using both the AGP and PCI buses, the review system can display no more than six ultrasound clips between two monitors (four on one monitor and two on the other) without frame rate degradation.

Additionally, many review systems store compressed ultrasound image clips in the memory unit of the review system for increased storage density. Typically, the CPU executes a software program to decompress these clips before sending them to the video display system for display. Because of power limitations, the CPU often cannot execute the decompression program quickly enough to avoid degradation in the frame rate of the displayed ultrasound clips.

Accordingly, there is a need for a method and system for simultaneously displaying diagnostic medical ultrasound image clips that will overcome the problems described above.

SUMMARY

The present invention is defined by the following claims, and nothing in this section should be taken as a limitation on those claims.

By way of introduction, the preferred embodiments described below include a method and system for simultaneously displaying diagnostic medical ultrasound image clips on one or more monitors without degradation in display frame rate. In one preferred embodiment, compressed ultrasound image frames are sent to a video display system for decompression. Because compressed image frames are sent, there is no degradation in frame rate caused by the bandwidth limitations of the CPU/video display system bus. Further, because the video display system decompress the compressed image frames faster than decompression software executed by a CPU, there is no degradation in frame rate caused by power limitations of the CPU. The video display system can also be used to control the frame rate, luminance, and size of individual ultrasound image clips. The preferred video display system described herein finds particular utility in ultrasound examinations performed in cardiac, radiological, obstetrical, and neo-natal ultrasound examinations.

The preferred embodiments will now be described with reference to the attached drawings.

DETAILED DESCRIPTION OF THE PRESENTLY PREFERRED EMBODIMENTS

System Overview

Figure 1:
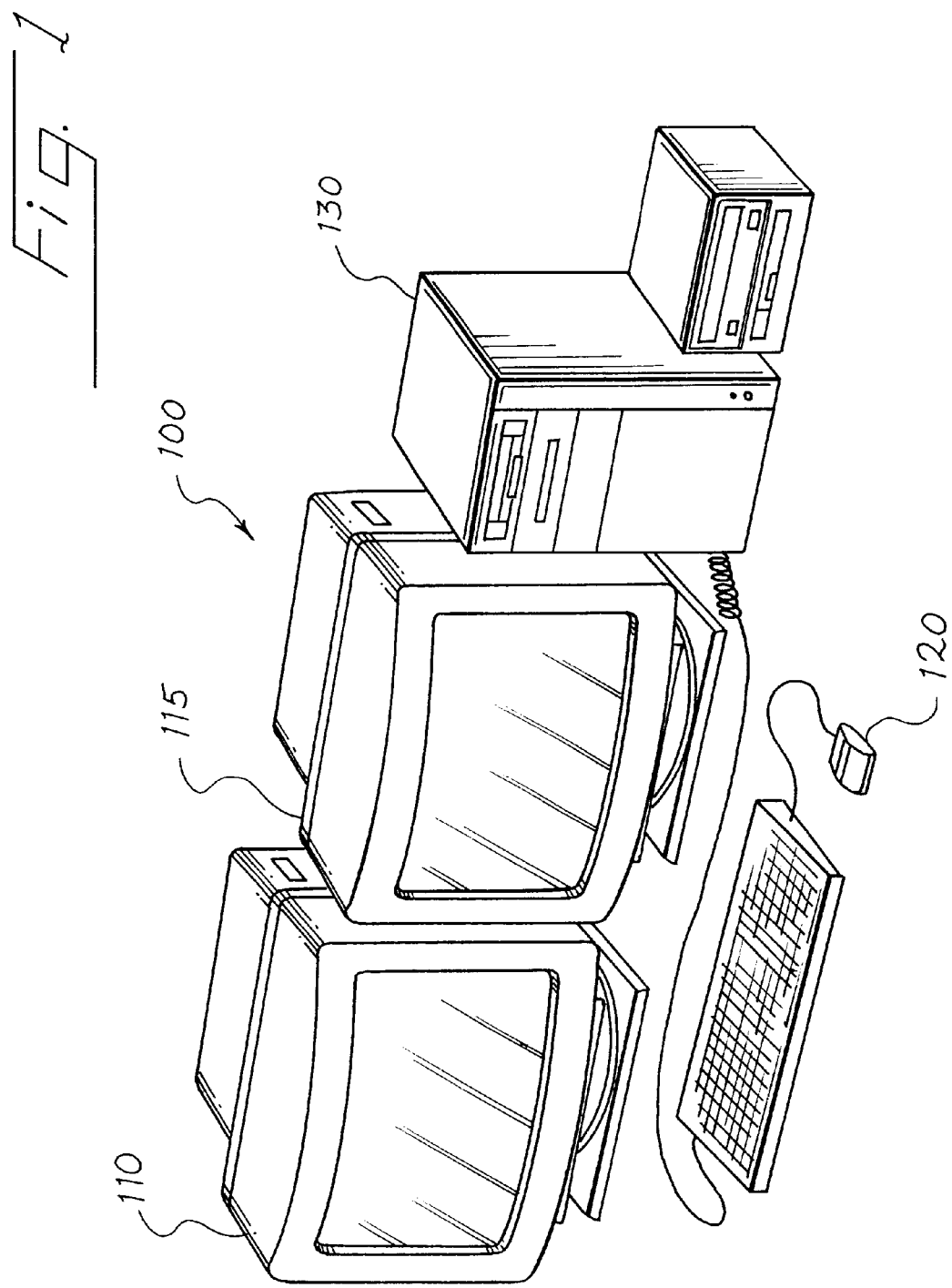
FIG. 1 is an illustration of an ultrasound image review system of a preferred embodiment.

Turning now to the drawings, FIG. 1 is an illustration of an ultrasound image review system 100 of a presently preferred embodiment. As used herein, the term "ultrasound image review system" refers to any device that can display digital ultrasound images. Ultrasound image review systems include, but are not limited to, ultrasound image review stations and ultrasound image acquisition devices. The ultrasound image review system 100 of FIG. 1 takes the form of an ultrasound image review station comprising a first and second monitor 110, 115, a mouse 120, and a computer unit 130. Although two monitors are shown in FIG. 1, the ultrasound image review system 100 can have only one monitor or can have three or more monitors.

Figure 2:
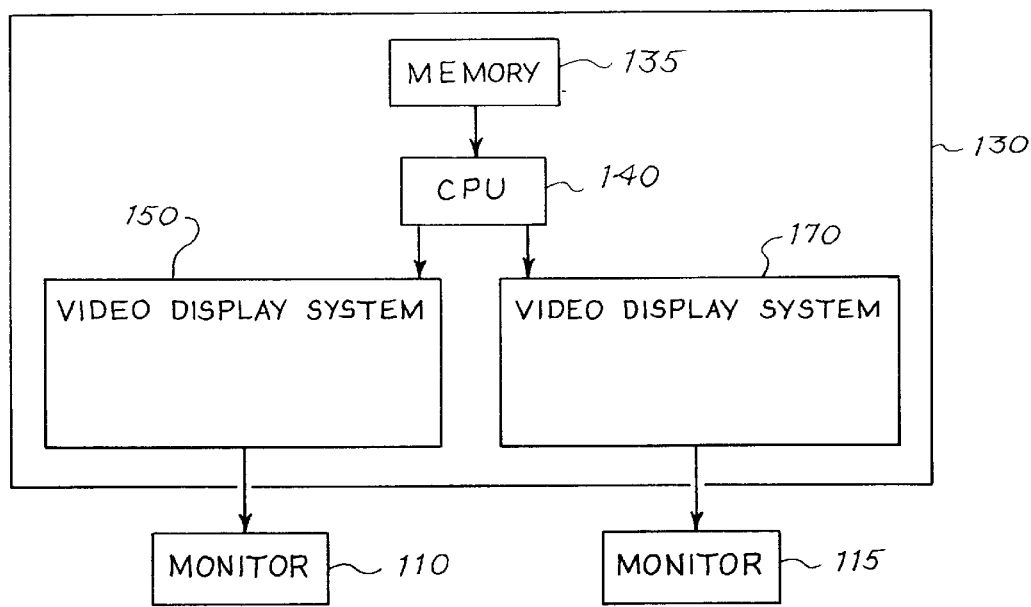
FIG. 2 is a block diagram of a computer for use in an ultrasound image review system of a preferred embodiment.

FIG. 2 is a block diagram of a preferred embodiment of the computer 130. Of course, the computer 130 may comprise components in addition to the ones shown in FIG. 2. Many, if not all, of these components may depend upon the particular computer used and are, therefore, not shown in FIG. 2. In this preferred embodiment, the computer 130 is a general purpose computer and comprises a memory unit 135 coupled with a CPU 140. As used herein, the term "coupled with" means directly coupled with or indirectly coupled with through one or more components. The CPU 140 is coupled with two video display systems 150, 170, which are coupled with monitors 110, 115, respectively. Additional monitors can be added to the system 100 by adding additional video display systems to the computer unit 130. As used herein, the term "video display system" refers to a self-contained system (i.e., independent of the CPU 140 of the image review system 100) that is operative to receive ultrasound data and render, from the ultrasound data, a viewable image on a monitor. In at least some of the preferred embodiments described below, the video display system takes the form of a video card whose high-speed hardware has the ability to receive compressed ultrasound data, decompress the compressed ultrasound data, perform image processing operations to the compressed and/or decompressed data, and render a viewable image on a monitor.

In operation, the review system 100 can be used to review ultrasound image clips that are digitally stored in the memory unit 135. As used herein, the term "ultrasound image clip" refers to a plurality of ultrasound image frames. An ultrasound image clip can be, for example, a series of ultrasound images that are acquired when an ultrasound transducer is swept across a patient. An ultrasound image clip can be transferred to the memory unit 135 from an ultrasound acquisition device via a direct connection between the review system and the acquisition device or via an indirect connection such as a network. Additionally, ultrasound image clips digitally saved on a portable medium, such as a magneto-optical disk, can be transferred into the memory unit 135 of the system 100.

The video display systems 150, 170 are operative to simultaneously display multiple ultrasound image clips without a degradation in frame rate. That is, the rate at which the frames of each ultrasound image clip are displayed ("the display frame rate") is the same as the rate at which the frames were acquired ("the acquired frame rate"). The following section describes video display system 150 in detail.

The Video Display System

Figure 3:
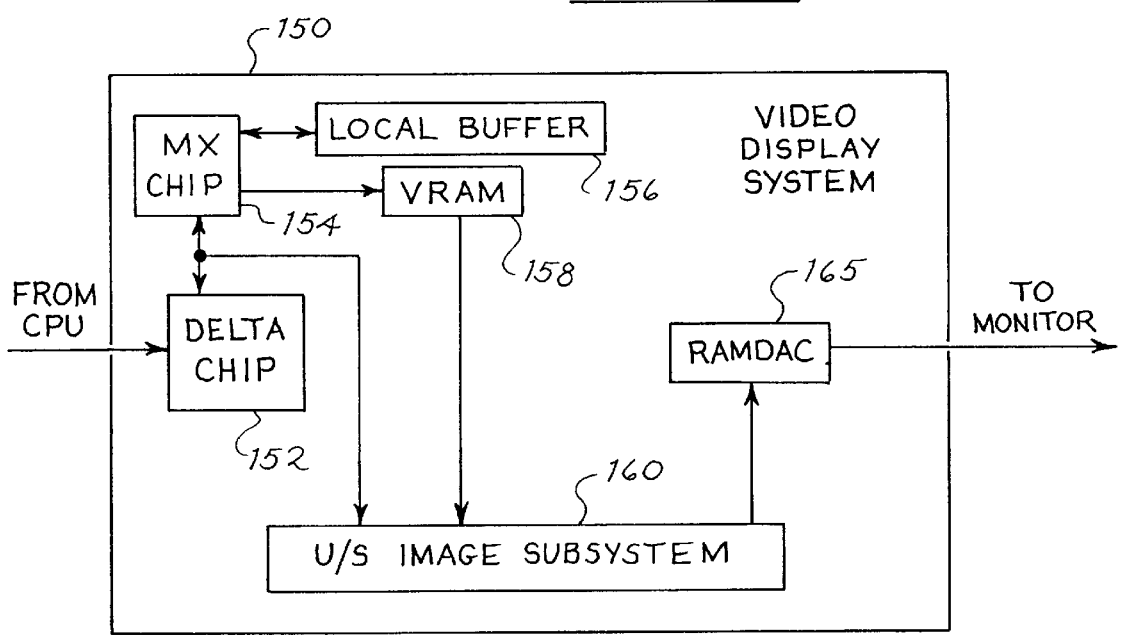
FIG. 3 is a block diagram of a video display system of a preferred embodiment.

FIG. 3 is a diagram of a preferred embodiment of video display system 150. In this preferred embodiment, the video display system 150 takes the form of a video card installed in the general-purpose computer 130 of the ultrasound image review system 100. Specifically, the video display system 150 comprises several off-the-shelf components for use with a Windows NT platform. In this preferred implementation, the video display system 150 comprises a delta and MX chip (preferably from 3 dlabs), a 16 MB DRAM local buffer 156, an 8 MB VRAM 158, and a RAMDAC 165 to convert digital images transferred from the CPU 140 to an analog signal for use by the monitor 110. It is important to note that this is merely one implementation and that many other implementations are possible.

Figure 4:
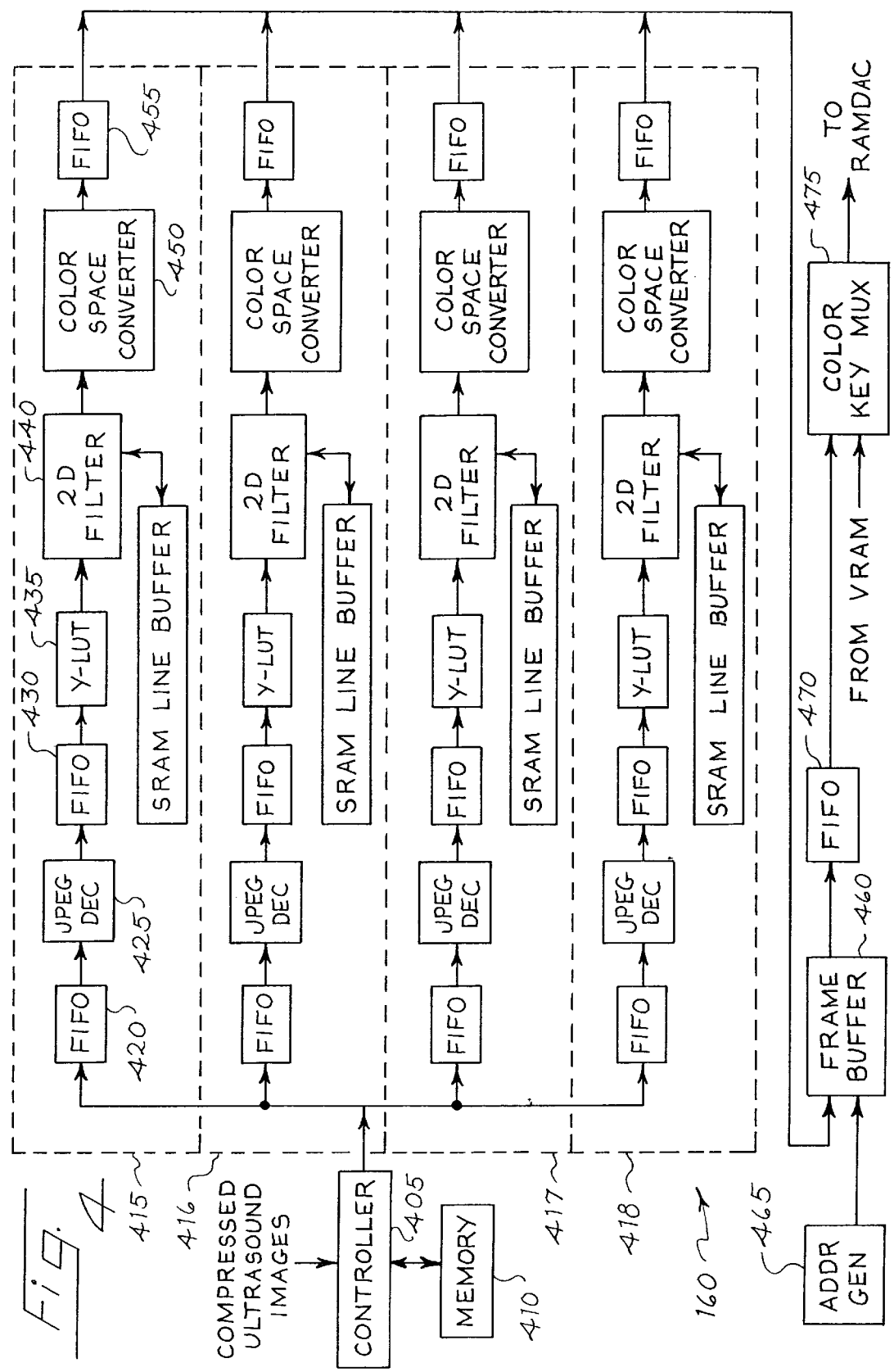
FIG. 4 is a block diagram of a preferred ultrasound image subsystem of the video display system of FIG. 3.

The video display system 150 also comprises an ultrasound image subsystem 160, which allows the simultaneous display of multiple ultrasound image clips. A preferred implementation of the ultrasound image subsystem 160 is shown in FIG. 4. When digital ultrasound image clips are received by the controller 405, which is preferably an IBM Power PC 403GCX microprocessor, the controller 405 stores the digital ultrasound image clips in the memory unit 410. In this preferred embodiment, the ultrasound image clips are transferred in a compressed, preferably JPEG, format from the CPU 140 to the video display system 150. Of course, other compression formats, including but not limited to the MPEG and wavelet formats, can be used. Because the clips are compressed, several clips can be transferred across the CPU/video display system bus without affecting the display frame rate. For example, a compressed ultrasound image clip may require a bandwidth of only 3 MB/sec instead of 30 MB/sec for an uncompressed image. In this way, 20 compressed ultrasound image clips (as compared to 2 uncompressed clips) can be sent across a 60 MB/sec bus without display frame rate degradation. Additionally, because the image clips are not decompressed by the CPU 140 before they are sent to the video display system 150, there is no frame rate degradation due to the CPU executing a decompression program. Further, storing the clips in a compressed format increases the storage density of the memory unit 410.

When instructed by the CPU 140 of the image review system 100, the controller 405 transfers compressed digital image frames to the ultrasound image display processing paths 415, 416, 417, 418. The four image paths 415, 416, 417, 418 shown in FIG. 4 are operative to simultaneously display four image clips on a monitor. The ultrasound image subsystem 160 is expandable in that additional image paths can be added. For example, a fifth image path can be added so that five image clips can be simultaneously displayed. Each of the image paths 415, 416, 417, 418 is operative to decompress compressed ultrasound image frames of an image clip, adjust the luminance of an image frame, adjust the size of an image frame, and convert the image frame into a color space suitable for digital-to-analog conversion by the RAMDAC 165. Because each image clip is processed by a different path, the luminance and size of each clip can be individually controlled. To illustrate this process, one of the paths (path 415) will be described below.

Path 415 comprises a first FIFO 420, a JPEG decoder 425 (preferably a 29.5 MHz Zoran PN ZR36060 JPEG CODEC), a second FIFO 430, a Y look-up table 435, a two-dimensional filter 440 with a corresponding SRAM line buffer 445, a color space converter 450, and a third FIFO 455. Each of the FIFOs 420, 430, 455 is used as a buffer to ensure that the image frames are processed at a constant rate. As a compressed image frame enters the path 415, the JPEG decoder 425 decompresses the image frame. Because a hardware component is used instead of a software program executed by the CPU, an image frame can be decompressed without degrading the frame rate of the displayed image clip.

Each pixel in the decompressed frame is associated with a YUV value; where the Y component corresponds to the luminance of the pixel and the UV component corresponds to the color of the pixel. The controller 405 can change the luminance of any image frame by adjusting the Y value in the Y look-up table 435. Additionally, the controller 405 can change the size of the image frame by instructing the two-dimensional filter 440 and associated SRAM line buffer 445 to scale the image frame to a specific size. For example, the controller 405 can instruct the two-dimensional filter 440 to scale a full-size image frame to a quarter-size image frame. Next, the color space converter 450 converts each pixel in the image frame from a YUV value to an RGB value, which is recognizable by the RAMDAC 165.

Figure 5:
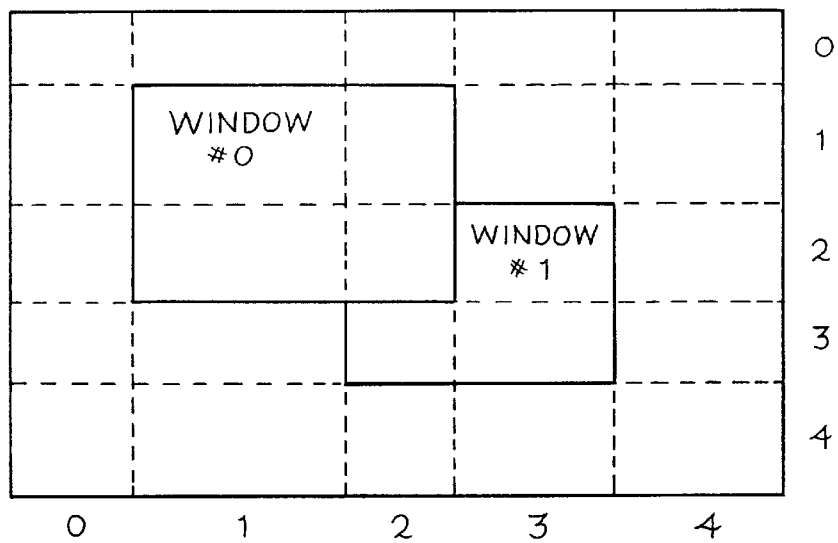
FIG. 5 is a diagram showing a screen display of a preferred embodiment.
Figure 6:
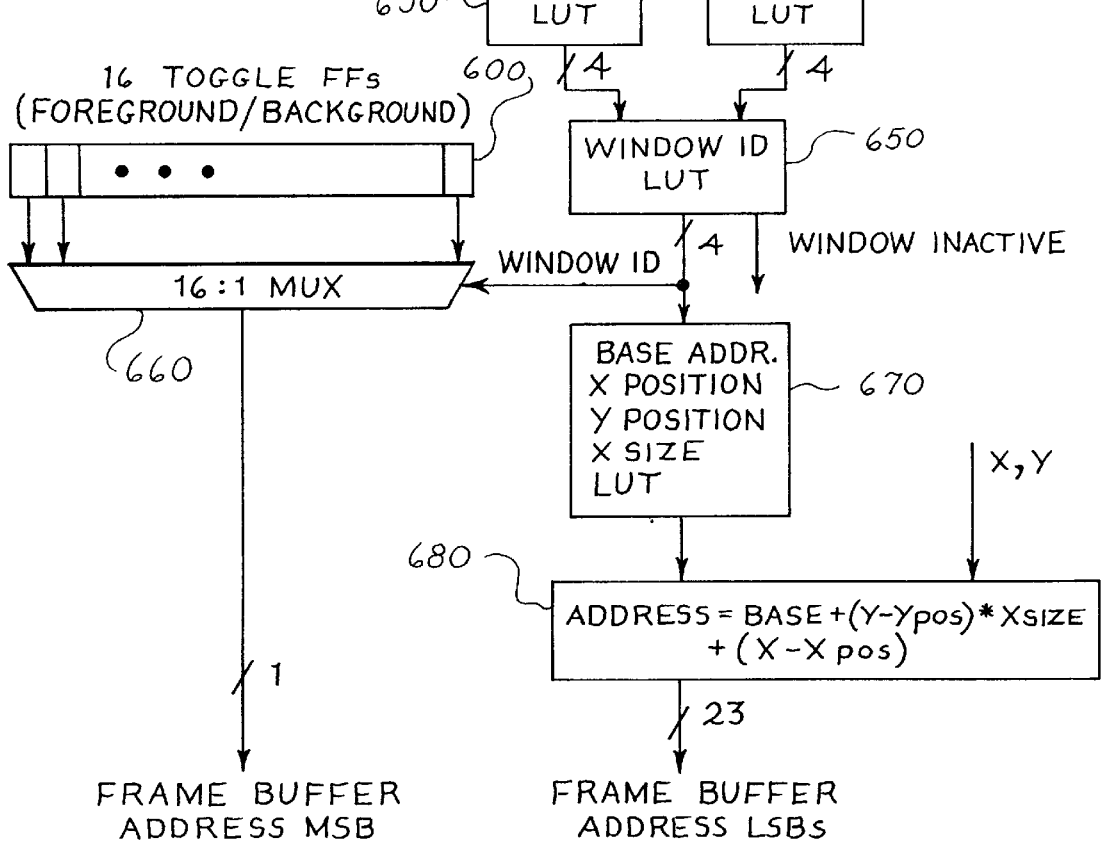
FIG. 6 is a diagram showing a preferred operation of the frame buffer of FIG. 4.

The processed image frames from each path are then written into the frame buffer 460, which preferably comprises six 1 MB×16 bit SDRAMs organized as 1 MB×96 bits. The ultrasound image subsystem 160 allows hardware-controlled double buffering in the frame buffer 460 on a window-by-window basis, and the address generator 465 ensures that each image pixel will be placed in the proper location. FIGS. 5 and 6 illustrate this double-buffering method. FIG. 5 shows two windows (Window #0 and Window #1) on a video display. By projecting the horizontal edges of the windows onto the vertical axis and the vertical edges onto the horizontal axis, the display is divided into regions, each characterized by a two-dimensional x-y ID. Additionally, each window is assigned an ID. Windows may cover multiple regions and may overlap. Window #0 and Window #1 overlap in region (2,2).

Data received from the image display processing paths are written to the frame buffer 460 in a linear fashion, starting at the background base address for the particular window to which it is assigned. When the entire frame is written, a flag is set, causing the foreground/background toggle flip-flop 600 associated with that window to toggle during the following vertical retrace interval (FIG. 6). For a 1600×1200 display, 11 bits are required to represent the horizontal and vertical dimensions. For cost and feasibility reasons, it is preferred to use only 9 bits, allowing window placement to a 4-pixel resolution. The output of the horizontal and vertical counters 610, 620 are used as inputs to the horizontal and vertical look-up tables 630, 640. The outputs of these look-up tables 630, 640 are applied to a Window ID look-up table 650, that generates a Window ID value. In this preferred embodiment, the Window ID is 4 bits, allowing for 16 windows. The Window ID look-up table 650 also generates a window inactive bit that indicates when there is no image data associated with a region. The Window ID is applied to a 16:1 multiplexor 660 to select the appropriate foreground/background toggle flip-flop 600 to use as the frame buffer address most-significant bit. The Window ID is also used to index a base address look-up table 670, the output of which is used to calculate the linear address with an address calculator 680. That address is used to read image data from the appropriate foreground region of the frame buffer 460.

Turning again to FIG. 4, another FIFO 470 is used as a buffer between the frame buffer 460 and the color key multiplexor 475. The color key multiplexor 475 controls whether a pixel from the frame buffer 460 or from the VRAM 158 will be sent to the RAMDEC 165 for display. The color key multiplexor 475 is sensitive to a specific color (e.g., blue) received from the VRAM 158. If the color key multiplexor 475 receives a pixel of that specific color from the VRAM 158, it will send the image pixel from the frame buffer 460 to the RAMDAC 165. Otherwise, the pixel from the VRAM 158 will be sent to the RAMDAC 165. The RAMDAC 165 then converts the pixel from a digital value to an analog signal, which the monitor uses to generate a display pixel.

There are several advantages to using the video display system described above. Because compressed image frames are sent to the video display system, there is no degradation in frame rate caused by the bandwidth limitations of the CPU/video display system bus. Further, because the hardware of the ultrasound image subsystem 160 decompress the compressed image frames faster than decompression software executed by the CPU, there is no degradation in frame rate caused by the CPU.

Another advantage associated with the preferred embodiments described above is that because each ultrasound display subsystem can be expanded to include several image display processing paths, more than four clips can be simultaneously displayed on one monitor without degradation in frame rate. To display more than four clips, each clip can be scaled equally (e.g., 5 image clips each scaled to a fifth-size image). Alternatively, because each clip can be individually scaled, one or more clips can be displayed at a larger size than the others. This may be especially important when a physician needs to study one particular clip in a larger scale than the other clips. Because image clips can be displayed in an overlapping fashion, image clips can be added without necessarily scaling the images. For example, if five clips are shown on a monitor, each clip can be reduced to a fifth-size image so each of the clips would fit on the monitor without overlap. Alternatively, each of the five clips can be displayed as quarter-sized images with, for example, four of the clips being displayed in each of the four quadrants of the monitor and one of the clips partially overlapping each of those four clips.

Yet another advantage associated with the preferred embodiments described above is that multiple monitors can be used without a degradation in display frame rate. Because the preferred image review system has an expandable architecture that allows for multiple display systems, multiple monitors can be used. Since each of the preferred display systems is responsible for decompressing and displaying the images sent to it, there is no degradation in display frame rate as additional video display systems and monitors are added. This allows for new ultrasound applications that require the simultaneous display of, for example, at least four image clips on at least two monitors. Some of these new applications are described below.

An additional advantage is that the video display system can individually control the frame rate of each of the image clips. As described above, the controller 405 sends the image frames from the memory unit 410 to a particular path in response from a command from the CPU 140. To control the frame rate of any particular clip, the controller 405 adjusts the rate at which image frames are sent to the path. For example, to decrease the display frame rate of the clips being processed by the first path 415 to 50% of the display frame rate of the clips being processed by the other paths 416, 417, 418, the controller 405 can deliver one frame to the first path 415 for every two images it delivers to the other paths 416, 417, 418. Also, the controller 405 can adjust the luminance of any frame of any clip by changing the values in the Y look-up table of any path. This may be especially important when increasing the luminance of all the clips would improve the display of one clip but would degrade the display of the others.

Although the preferred embodiments above were described in terms of compressed image frames, these advantages can also be realized with uncompressed image frames by using a video display system with a sufficiently large memory unit. In this alternative embodiment, the CPU 140 transfers uncompressed ultrasound image clips to the memory unit 410 once and thereafter sends a command to the controller 405 to display the clips stored in the memory unit 410. Because of the bandwidth limitations of the bus between the CPU 140 and the video display system 150, loading all the image clips into the memory unit 410 of the ultrasound image subsystem 160 may be a time-consuming task. However, the images need only be sent across the limited-bandwidth bus once. Thereafter, the CPU 140 merely sends a short message instructing the subsystem controller to display the stored clip each time the ultrasound clip is to be played.

In another alternative embodiment, image processing operations, some of which are conventionally performed with software executed by the CPU of the image review system, are performed by the video display system. Each image path can have its own image processing component. Alternatively, one or more image paths can feed into a single image processing component. In situations in which compressed ultrasound images are sent to the video display system, the image processing component can be located before or after the decompression component, allowing image processing to be performed on either compressed or decompressed images. One such example is changing the size of (i.e., scaling) an ultrasound image. Other examples of image processing operations that can be performed by the video display system are described in the following patent applications, which are assigned to the assignee of the present patent application and are hereby incorporated by reference: "Medical Diagnostic Ultrasound System and Method for Transform Ultrasound Processing," U.S. Pat. No. 6,042,545, issued Mar 28, 2000 and "Ultrasonic System and Method for Compounding," Ser. No. 09/199,945 filed Nov. 25, 1998.

Applications

The preferred embodiments described above find particular utility in ultrasound examinations performed in cardiac examinations. In a cardiac examination, several views of the heart can be imaged. For example, the long axis, short axis, apical four chamber, and apical two chamber views can be imaged with a single transducer during different heart cycles or with multiple transducers during a single heart cycle. When multiple ultrasound image clips are simultaneously displayed, a physician can have a better perspective of the heart than if he were to review only a single ultrasound image clip. Further, displaying more than four ultrasound image clips on one monitor and/or displaying several clips on multiple monitors provides the physician with a three-dimensional-like view of the heart. For example, with the simultaneous display on two monitors of eight ultrasound clips representing the various views of the heart, a physician can visualize the entire volume of the heart without using complex three-dimensional ultrasound equipment.

If the first frame displayed for each of the ultrasound clips was not acquired at the same part of the heart cycle, the displayed ultrasound clips will not be synchronized. Accordingly, it is preferred that the first frame displayed for each ultrasound clip be the frame acquired at the R-wave—the electrical voltage shown on an electrocardiogram that indicates the beginning of systole. Synchronizing the first frame in each of the clips may not be sufficient to synchronize the display if the ultrasound clips were acquired over different heart cycles. For example, if some ultrasound clips were acquired while the patient was at rest and other ultrasound clips were acquired when the patient's heart rate was accelerated during a stress echo test, the display will be out of synch after several frames of the clip are displayed. To overcome this problem, it is preferred that the frame rate of the ultrasound clips be adjusted so that the image frames acquired at the R-wave of each of the clips are displayed simultaneously. For example, if one of eight ultrasound clips were acquired during a stress echo test, that ultrasound clip can be displayed at a lower frame rate so the frames from each clip acquired at the R-wave are displayed at the same time, making it appear as if each of the clips were acquired during the same heart cycle.

The preferred embodiments described above also find particular utility in ultrasound examinations in the radiological (e.g., abdominal organs), obstetrical (e.g., a fetus from conception to birth date), and neo-natal (e.g., newborn babies) fields. In these examinations, several static ultrasound images (e.g., of fetal anatomy or neo-natal heads) are acquired and later reviewed by a physician. Although these examinations provide a physician with useful information, the information is inherently limited by the number of static images that are available for review by the physician. Additionally, acquiring enough static images for a physician to make a diagnosis is often a time-intensive task.

By using the preferred embodiments described above, the sonographer can take a sweep of the organ of interest instead of several static ultrasound frames, thereby accelerating the performance of the ultrasound examination. Additionally, simultaneously displaying several ultrasound clips can provide the physician with a better perspective and deeper understanding of the examined organ as compared to the simultaneous display of static images. Further, with static images, the physician is restricted to the limited sampling of static images acquired by the sonographer. Because more frames are acquired with these preferred embodiments, the physician can effectively rescan the patient by selecting to view one of the many frames acquired in a clip.

Preferably, each sweep is taken over the same amount of time (i.e., each clip is of the same temporal duration). If the sweeps are not of the same temporal duration, the displayed ultrasound clips will be out of synch when the clips are looped. To synchronize the playback of these clips, it is preferred that the frame rate of the ultrasound clips be adjusted so that the first and last frame of each ultrasound clip are displayed at the same time. Alternatively, the looping of each clip can be delayed until the last frame of the longest clip is displayed.

It is intended that the foregoing detailed description be understood as an illustration of selected forms that the invention can take and not as a definition of the invention. It is only the following claims, including all equivalents, that are intended to define the scope of this invention.

What is claimed is:

1. A method for simultaneously displaying a plurality of ultrasound image clips with an ultrasound image review system comprising a first and second video display system coupled with a first and second monitor, respectively, the method comprising:

(a) acquiring at least seven ultrasound image clips each comprising a respective plurality of ultrasound image frames acquired at a respective acquisition frame rate;

(b) storing said at least seven ultrasound image clips;

(c) providing at least four ultrasound image clips of said at least seven ultrasound image clips to the first video display system of the ultrasound image review system;

(d) providing at least three ultrasound image clips of said at least seven ultrasound image clips to the second video display system of the ultrasound image review system; and (e) simultaneously displaying said at least four ultrasound image clips on the first monitor and said at least three ultrasound image clips on the second monitor, the respective plurality of ultrasound image frames of said at least four ultrasound image clips and said at least three ultrasound image clips being displayed at their respective acquisition frame rates.

2. A method for simultaneously displaying a plurality of ultrasound image clips with an ultrasound image review system comprising a first and second video display system coupled with a first and second monitor, respectively, the method comprising:

(a) receiving at least four ultrasound image clips each comprising a respective plurality of ultrasound image frames acquired at a respective acquisition frame rate;

(b) receiving at least three additional ultrasound image clips each comprising a respective plurality of ultrasound image frames acquired at a respective acquisition frame rate; and (c) simultaneously displaying said at least four ultrasound image clips on a first monitor and said at least three ultrasound image clips on a second monitor, the respective plurality of ultrasound image frames of said at least four ultrasound image clips and said at least three ultrasound image clips being displayed at their respective acquisition frame rates.

3. The method of claim 2, wherein at least two ultrasound image clips on at least one of the monitors overlap.

4. The method of claim 2, wherein an ultrasound image clip is characterized by a luminance, and wherein the method further comprises adjusting the luminance of at least one of the image clips displayed on one of the monitors.

5. The method of claim 2, wherein an ultrasound image clip is characterized by an image size, and wherein the method further comprises adjusting the image size of at least one of the image clips displayed on one of the monitors.

6. The method of claim 2, wherein an ultrasound image clip is characterized by a display frame rate, and wherein the method further comprises adjusting the display frame rate of at least one of the image clips displayed on one of the monitors.

7. A method for simultaneously displaying a plurality of ultrasound image clips with an ultrasound image review system comprising a first and second video display system coupled with a first and second monitor, respectively, the method comprising:
(a) acquiring a first and second ultrasound image clip each comprising a respective plurality of ultrasound image frames acquired at a respective acquisition frame rate;
(b) storing said first and second ultrasound image clips in a compressed format;
(c) providing said first ultrasound image clip in a compressed format to the first video display system of the ultrasound image review system;
(d) providing said second ultrasound image clip in a compressed format to the second video display system of the ultrasound image review system;
(e) decompressing said first ultrasound image clip with the first video display system;
(f) decompressing said second ultrasound image clip with the second video display system; and
(g) simultaneously displaying said first ultrasound image clip on the first monitor and said second ultrasound image clip on the second monitor, the respective plurality of ultrasound image frames of said first and second ultrasound image clips being displayed at their respective acquisition frame rates.

8. A method for simultaneously displaying a plurality of ultrasound image clips with an ultrasound image review system comprising a first and second video display system coupled with a first and second monitor, respectively, the method comprising:
(a) receiving a first ultrasound image clip in a compressed format with a first video display system;
(b) receiving a second ultrasound image clip in a compressed format with a second video display system, said first and second ultrasound image clips each comprising a respective plurality of ultrasound image frames acquired at a respective acquisition frame rate;
(c) decompressing said first ultrasound image clip with the first video display system;
(d) decompressing said second ultrasound image clip with the second video display system; and
(e) simultaneously displaying said first ultrasound image clip on the first monitor and said second ultrasound image clip on the second monitor, the respective plurality of ultrasound image frames of said first and second ultrasound image clips being displayed at their respective acquisition frame rates.

9. An ultrasound image review system comprising:
a first monitor;
a second monitor;
a first video display system, coupled with the first monitor, comprising:
a first memory unit operative to store a first ultrasound image clip in a compressed format;
a first ultrasound image display processing path operative to decompress said compressed first ultrasound image clip; and
a first controller coupled with the first memory unit and first ultrasound image display processing path;
a second video display system, coupled with the second monitor, comprising:
a second memory unit operative to store a second ultrasound image clip in a compressed format;
a second ultrasound image display processing path operative to decompress said compressed second ultrasound image clip;
a second controller coupled with the second memory unit and second ultrasound image display processing path;
said first and second ultrasound image clips comprising a respective plurality of ultrasound image frames acquired at a respective acquisition frame rate; and
said first and second controllers operative to simultaneously display said first and second ultrasound image clips on the first and second monitors, respectively, such that the respective plurality of ultrasound image frames of said first and second ultrasound image clips are displayed at their respective acquisition frame rates.

10. A method for simultaneously displaying ultrasound image clips, the method comprising:
(a) displaying at least one ultrasound image clip on a first display device; and
(b) simultaneously displaying at least one ultrasound image clip on a second display device;
wherein the at least one ultrasound image clip displayed on the first display device comprises at least three ultrasound image clips and wherein the at least one ultrasound image clip simultaneously displayed on the second display device comprises at least four ultrasound image clips.

11. The invention of claim 10, wherein the ultrasound image clips simultaneously displayed on the first and second display devices are displayed at their respective acquisition frame rates.

12. A method for simultaneously displaying ultrasound image clips, the method comprising:
(a) displaying at least one ultrasound image clip on a first display device; and
(b) simultaneously displaying at least one ultrasound image clip on a second display device;
wherein the at least one ultrasound image clip displayed on the first display device comprises at least two ultrasound image clips and wherein the at least one ultrasound image clip simultaneously displayed on the second display device comprises at least five ultrasound image clips.

13. The invention of claim 12, wherein the ultrasound image clips simultaneously displayed on the first and second display devices are displayed at their respective acquisition frame rates.

* * * * *